United States Patent [19]
Samain et al.

[11] Patent Number: 6,039,933
[45] Date of Patent: Mar. 21, 2000

[54] COSMETIC COMPOSITION PRESSURIZED IN AN AEROSOL DEVICE AND THE RESULTING FOAM

[75] Inventors: Henri Samain, Bièvres; Isabelle Cretois, Clichy, both of France

[73] Assignee: L'Oreal, Paris, France

[21] Appl. No.: 09/043,220

[22] PCT Filed: Jun. 30, 1997

[86] PCT No.: PCT/FR97/01163

§ 371 Date: Jun. 9, 1998

§ 102(e) Date: Jun. 9, 1998

[87] PCT Pub. No.: WO98/03148

PCT Pub. Date: Jan. 29, 1998

[30] Foreign Application Priority Data

Jul. 17, 1996 [FR] France .................. 96 08958

[51] Int. Cl.[7] ............... A61K 7/06; A61K 7/11; A61K 9/12
[52] U.S. Cl. ............. 424/47; 424/43; 424/70.11; 424/70.12; 424/70.19; 424/70.22
[58] Field of Search ............. 424/47, 43, 70.12, 424/70.19, 70.22, 70.24, 70.11

[56] References Cited

U.S. PATENT DOCUMENTS 5,620,684  4/1997  Dupuis .

FOREIGN PATENT DOCUMENTS

| | | |
|---|---|---|
| 0 635 258 | 1/1995 | European Pat. Off. . |
| 2 709 954 | 3/1995 | European Pat. Off. . |
| 2 709 955 | 3/1995 | European Pat. Off. . |
| 0 723 770 | 7/1996 | European Pat. Off. . |
| 1-180813 | 7/1989 | Japan . |
| 5-92911 | 4/1993 | Japan . |
| 6-100418 | 4/1994 | Japan . |
| 7-89830 | 4/1995 | Japan . |
| 95/32703 | 12/1995 | WIPO . |

*Primary Examiner*—Thurman K. Page
*Assistant Examiner*—Brian K. Seidleck
*Attorney, Agent, or Firm*—Finnegan, Henderson, Farabow, Garrett & Dunner, L.L.P.

[57] ABSTRACT

Pressurised cosmetic compositions provided in pressurised form in an aerosol device in the presence of a propellant, and capable of forming a foam, are disclosed. Said compositions comprise a cosmetically acceptable medium containing at least one binding polymer, at least one oxyalkylene silicone and at least 30 wt % of a water-soluble solvent having a boiling point lower than 85° C. Foams produced by the expansion in air of said cosmetic compositions are also disclosed. Furthermore, a method for cosmetically treating keratin fibres such as hair, wherein a foam produced by the expansion in air of said cosmetic composition is applied to said keratin fibres, is disclosed.

48 Claims, No Drawings

COSMETIC COMPOSITION PRESSURIZED IN AN AEROSOL DEVICE AND THE RESULTING FOAM

This application is a 371 of PCT/FR97/01163, filed on Jun. 30, 1997.

The invention relates to cosmetic compositions packaged in an aerosol device in the presence of a propellant and capable of forming a foam comprising, in a cosmetically acceptable medium, at least one fixing polymer, at least one oxyalkylenated silicone and at least 30% by weight of a water-soluble solvent having a boiling point of less than 85° C., to the resulting foams and to a process for the cosmetic treatment of keratinous fibres, such as hair or eyelashes, characterized in that it consists in applying, to keratinous fibres, the said foam resulting from the expansion in the air of the cosmetic composition as defined above.

Cosmetic compositions pressurized in aerosol devices, under conditions such that they can form a foam at the outlet of the device, are well known and are used in particular in the treatment of hair and/or of the skin. Such compositions will be known in the continuation of the description as "aerosol foam".

These foams generally make it possible to obtain a good distribution of the cosmetic compositions over the hair and they are, in addition, easy to use and more economical as regards the amount of product used in comparison with lotions.

These foams must be sufficiently stable not to liquefy quickly and must also disappear rapidly, either spontaneously or during the massaging which is used to make the composition penetrate and/or distribute over keratinous substances and more particularly hair.

Hair styling and/or form-retention foams generally contain at least one polymer, preferably an anionic, non-ionic or amphoteric polymer, which contributes fixing properties to the hair.

These polymers are generally non-foaming or weakly foaming and, in order to obtain an aerosol foam, it is thus necessary to add a foaming agent and/or an agent which improves the quality of the foam.

Unlike conventional aerosol fixing hair sprays, these compositions have the disadvantage of not allowing hair to be fixed in a shape which has already been prepared. Neither do they allow the hairstyle to be shaped while being simultaneously fixed. This is because these compositions are essentially aqueous and their application wets the hair and can thus not maintain the initial shape of the hairstyle. A subsequent blow-drying or drying is thus necessary in order to shape and fix the hairstyle. Moreover, the hair is generally stuck together in clumps and the hairstyle does not withstand mechanical deformations, such as wind or rubbing actions.

It is known that the presence of a solvent, such as ethanol, makes it possible to decrease the drying time of essentially aqueous compositions. However, it is also known that the presence of a large amount of ethanol does not allow compositions to be obtained in the foam form using the foaming polymers or surfactants conventionally used to form foams.

The aim of the present invention is thus to provide a composition which forms a foam at the outlet of an aerosol device, which is easily and quickly distributed and which makes it possible to fix a lock or a hairstyle in the desired shape without prolonged blow-drying or drying.

To this end, the Applicant Company has now just discovered that compositions comprising at least one fixing polymer, at least one oxyalkylenated silicone and at least 30% of a water-soluble solvent, such as ethanol, unexpectedly and surprisingly form, in the presence of a propellant, foams which result in particularly advantageous properties, in particular a fixing of the hairstyle and an improvement in the hold of the hairstyle over time. The hair has more volume, is glossy and exhibits a natural feel. The compositions also have the advantage of not dispersing particles in suspension in the atmosphere.

The subject of the present invention is thus a cosmetic composition in the pressurized state in an aerosol device in the presence of a propellant capable of forming a foam at the outlet of the said device, which is characterized in that it comprises, in a cosmetically acceptable medium, at least one fixing polymer, at least one oxyalkylenated silicone and at least 30% by weight, expressed with respect to the propellant-free composition, of a water-soluble solvent having a boiling point of less than 85° C.

Another subject of the invention is a cosmetic composition in the form of a foam, characterized in that it results from the expansion in the air of a composition as defined above.

Another subject of the invention is the use of an oxyalkylenated silicone as a foaming agent for compositions pressurized in aerosol form which are capable of forming a foam and which comprise at least one fixing polymer and at least 30% by weight of a water-soluble solvent having a boiling point of less than 85° C.

Other characteristics, aspects, objects and advantages of the invention will become still more clearly apparent on reading the description and examples which follow.

The compositions according to the invention thus contain at least one fixing polymer. Fixing polymer is understood to mean any polymer having the function of temporarily fixing the shape of the hairstyle. Fixing power of the composition containing such a fixing polymer is understood to denote the ability of the composition to give the hair a cohesion such that the initial shaping of the hairstyle to which the composition is applied is retained.

According to the invention, any fixing polymer known per se can be used. A fixing polymer chosen from anionic, cationic, amphoteric or non-ionic polymers and their mixtures can be used in particular. The fixing polymers can be used in the dissolved form or in the form of dispersions of solid or liquid particles of polymer.

The cationic fixing polymers which can be used according to the present invention are preferably chosen from polymers containing primary, secondary, tertiary and/or quaternary amine groups forming part of the polymer chain or directly bonded to the latter and having a number-average molecular weight of between 500 and approximately 5,000,000 and preferably between 1000 and 3,000,000.

Mention may more particularly be made, among these polymers, of the following cationic polymers:

(1) homopolymers or copolymers derived from acrylic or methacrylic esters or amides containing at least one of the units of following formulae:

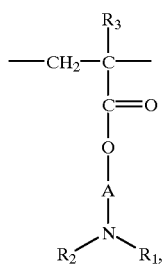

(A)

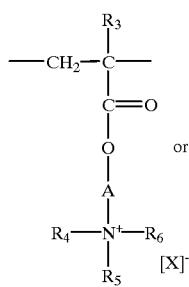

(B)

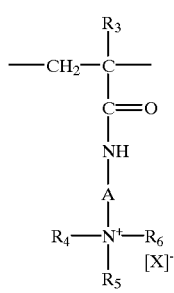

(C)

in which:

R$_3$ denotes a hydrogen atom or a CH$_3$ radical,

A is a linear or branched alkyl group containing 1 to 6 carbon atoms or a hydroxyalkyl group containing 1 to 4 carbon atoms;

R$_4$, R$_5$ and R$_6$, which are identical or different, represent an alkyl group having from 1 to 18 carbon atoms or a benzyl radical, R$_1$ and R$_2$ represent hydrogen or an alkyl group having from 1 to 6 carbon atoms, X denotes a methyl sulphate anion or a halide, such as chloride or bromide.

The copolymers of the family (1) additionally contain one or more units deriving from comonomers which can be chosen from the family of acrylamides, methacrylamides, diacetone acrylamides, acrylamides and methacrylamides substituted on the nitrogen by lower alkyls, acrylic or methacrylic acids and their esters, vinyllactams, such as vinylpyrrolidone or vinylcaprolactam, or vinyl esters.

Thus, mention may be made, among these copolymers of the family (1), of:

copolymers of acrylamide and of dimethylaminoethyl methacrylate quaternized with dimethyl sulphate or with a dimethyl halide, such as that sold under the name Hercofloc by the company Hercules, copolymers of acrylamide and of methacryloyloxyethyltrimethylammonium chloride described, for example, in Patent Application EP-A-080,976 and sold under the name Bina Quat P 100 by the company Ciba-Geigy, copolymers of acrylamide and of methacryloyloxyethyltrimethylammonium methyl sulphate sold under the name Reten by the company Hercules, optionally quaternized vinylpyrrolidone/dialkyl-aminoalkyl acrylate or methacrylate copolymers, such as the products sold under the name "Gafquat" by the company ISP, such as, for example, "Gafquat 734" or "Gafquat 755", or else the products named "Copolymer 845, 958 and 937". These polymers are described in detail in French Patents 2,077,143 and 2,393,573, dimethylaminoethyl methacrylate/vinylcaprolactam/vinylpyrrolidone terpolymers, such as the product sold under the name Gaffix VC 713 by the company ISP, and quaternized dimethylaminopropyl methacryl-amide/vinylpyrrolidone copolymers, such as in particular the product sold under the name "Gafquat HS 100" by the company ISP.

(2) Quaternized polysaccharides, described more particularly in U.S. Pat. Nos. 3,589,578 and 4,031,307, such as guar gums containing cationic trialkylammonium groups.

Such products are sold in particular under the trade names Jaguar C13 S, Jaguar C 15 and Jaguaer C 17 by the company Meyhall.

(3) Quaternary copolymers of vinylpyrrolidone and of vinylimidazole;

(4) chitosans or their salts;

the salts which can be used are in particular chitosan acetate, lactate, glutamate, gluconate or pyrrolidonecarboxylate.

Mention may be made, among these compounds, of the chitosan having a degree of deacetylation of 90.5% by weight sold under the name Kytan Crude Standard by the company Aber Technologies or the chitosan pyrrolidonecarboxylate sold under the name Kytamer PC by the company Amerchol.

The anionic fixing polymers generally used are polymers containing groups derived from carboxylic, sulphonic or phosphoric acid and have a number-average molecular weight of between approximately 500 and 5,000,000.

1) The carboxyl groups are contributed by unsaturated carboxylic mono- or diacid monomers such as those corresponding to the formula:

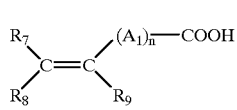

(I)

in which n is an integer from 0 to 10, A$_1$ denotes a methylene group, optionally bonded to the carbon atom of the unsaturated group or to the neighbouring methylene group when n is greater than 1 via a heteroatom, such as oxygen or sulphur, R$_7$ denotes a hydrogen atom or a phenyl or benzyl group, R$_8$ denotes a hydrogen atom or a lower alkyl or carboxyl group, and R$_9$ denotes a hydrogen atom, a lower alkyl group or a —CH$_2$—COOH, phenyl or benzyl group.

In the abovementioned formula, a lower alkyl radical preferably denotes a group having 1 to 4 carbon atoms and in particular methyl and ethyl.

The preferred anionic fixing polymers containing carboxyl groups according to the invention are:

A) Homo- or copolymers of acrylic or methacrylic acid or their salts and in particular the products sold under the names Versicol E or K by the company Allied Colloid and Ultrahold by the company BASF, the copolymers of acrylic acid and of acrylamide sold in the form of their sodium salt under the names Reten 421, 423 or 425 by the Company Hercules or the sodium salts of polyhydroxycarboxylic acids.

B) Copolymers of acrylic or methacrylic acid with a monoethylenic monomer, such as ethylene, styrene, vinyl esters or esters of acrylic or methacrylic acid, optionally grafted onto a polyalkylene glycol, such as polyethylene glycol, and optionally crosslinked. Such polymers are described in particular in French Patent 1,222,944 and German Application 2,330,956, the copolymers of this type containing, in their chain, an optionally N-alkylated and/or -hydroxyalkylated acryl-amide unit, such as described in particular in Luxembourgian Patent Applications 75370 and 75371 or provided under the name Quadramer by the Company American Cyanamid. Mention may also be made of copolymers of acrylic acid and of $C_1$–$C_4$ alkyl methacrylate and terpolymers of vinylpyrrolidone, of acrylic acid and of $C_1$–$C_{20}$ alkyl methacrylate, for example lauryl methacrylate, such as that sold by the company ISP under the name Acrylidone LM, and methacrylic acid/ethyl acrylate/tert-butyl acrylate terpolymers, such as the product sold under the name Luvimer 100 P by the company BASF.

C) Copolymers derived from crotonic acid, such as those containing, in their chain, vinyl acetate or propionate units and optionally other monomers, such as allyl or methallyl esters, vinyl ether or vinyl ester of a linear or branched saturated carboxylic acid containing a long hydrocarbon chain, such as those containing at least 5 carbon atoms, it optionally being possible for these polymers to be grafted and crosslinked, or alternatively another vinyl, allyl or methallyl ester of an α- or β-cyclic carboxylic acid monomer. Such polymers are described, inter alia, in French Patents 1,222,944, 1,580,545, 2,265,782, 2,265,781, 1,564,110 and 2,439,798. Commercial products coming within this class are the Resins 28-29-30, 26-13-14 and 28-13-10 sold by the company National Starch.

D) Copolymers derived from $C_4$–$C_8$ monounsaturated carboxylic acids or anhydrides chosen from:

copolymers comprising (i) one or more maleic, fumaric or itaconic acids or anhydrides and (ii) at least one monomer chosen from vinyl esters, vinyl ethers, vinyl halides, phenylvinyl derivatives, or acrylic acid and its esters, the anhydride functional groups of these copolymers optionally being monoesterified or monoamidated; such polymers are described in particular in Patents U.S. Pat. Nos. 2,047,398, 2,723,248 and 2,102,113 and Patent GB 839, 805. Commercial products are in particular those sold under the names Gantrez AN or ES by the company ISP.

copolymers comprising (i) one or more maleic, citraconic or itaconic anhydride units and (ii) one or more monomers chosen from allyl or methallyl esters, optionally containing one or more acrylamide, methacrylamide, α-olefin, acrylic or methacrylic ester, acrylic or methacrylic acid, or vinylpyrrolidone groups in their chain, the anhydride functional groups of these copolymers optionally being monoesterified or monoamidated.

These polymers are, for example, described in French Patents 2,350,384 and 2,357,241 of the Applicant Company.

E) Polyacrylamides containing carboxylate groups.

The polymers comprising sulpho groups are polymers containing vinylsulphonic, styrenesulphonic, naphthalenesulphonic or acrylamidoalkylsulphonic units.

These polymers can in particular be chosen from:

salts of polyvinylsulphonic acid having a molecular weight of between approximately 1000 and 100,000, as well as copolymers with an unsaturated comonomer, such as acrylic or methacrylic acids and their esters as well as acrylamide or its derivatives, vinyl ethers and vinylpyrrolidone.

salts of polystyrenesulphonic acid, the sodium salts having a molecular weight of approximately 500,000 and of approximately 100,000 sold respectively under the names Flexan 500 and Flexan 130 by National Starch. These compounds are described in Patent FR 2,198,719.

salts of polyacrylamide sulphonic acids, such as those mentioned in Patent U.S. Pat. No. 4,128,631 and more particularly the polyacrylamidoethylpropanesulphonic acid sold under the name Cosmedia Polymer HSP 1180 by Henkel.

According to the invention, the anionic fixing polymers are preferably chosen from acrylic acid copolymers, such as the acrylic acid/ethyl acrylate/N-tert-butylacrylamide terpolymers sold in particular under the name Ultrahold Strong by the company BASF, copolymers derived from crotonic acid, such as the vinyl acetate/vinyl tert-butylbenzoate/crotonic acid terpolymers and the crotonic acid/vinyl acetate/vinyl neododecanoate terpolymers sold in particular under the name Resin 28-29-30 by the company National Starch, polymers derived from maleic, fumaric or itaconic acids or anhydrides with vinyl esters, vinyl ethers, vinyl halides, phenylvinyl derivatives, or acrylic acid and its esters, such as the monoesterified methyl vinyl ether/maleic anhydride copolymers sold, for example, under the name Gantrez by the company ISP, copolymers of methacrylic acid and of methyl methacrylate sold under the name Eudragit L by the company Rohm Pharma, copolymers of methacrylic acid and of ethyl acrylate sold under the name Luvimer MAEX or MAE by the company BASF and vinyl acetate/crotonic acid copolymers sold under the name Luviset CA 66 by the company BASF and vinyl acetate/crotonic acid copolymers grafted by polyethylene glycol sold under the name Aristoflex A by the company BASF.

The most particularly preferred anionic fixing polymers are chosen from the monoesterified methyl vinyl ether/maleic anhydride copolymers sold under the name Gantrez ES 425 by the company ISP, the acrylic acid/ethyl acrylate/N-tert-butylacrylamide terpolymers sold under the name Ultrahold Strong by the company BASF, the copolymers of methacrylic acid and of methyl methacrylate sold under the name Eudragit L by the company Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, the copolymers of methacrylic acid and of ethyl acrylate sold under the name Luvimer MAEX or MAE by the company BASF or the vinylpyrrolidone/acrylic acid/lauryl methacrylate terpolymers sold under the name Acrylidone LM by the company ISP.

The amphoteric fixing polymers which can be used in accordance with the invention can be chosen from polymers containing B and C units distributed randomly in the polymer chain, where B denotes a unit deriving from a monomer containing at least one basic nitrogen atom and C denotes a unit deriving from an acidic monomer containing one or more carboxyl or sulpho groups or else B and C can denote groups deriving from zwitterionic carboxybetaine or sulphobetaine monomers; B and C can also denote a cationic polymer chain containing primary, secondary, tertiary or quaternary amine groups, in which at least one of the amine groups carries a carboxyl or sulpho group connected via a hydrocarbon radical, or else B and C form part of a chain of a polymer containing an α,β-dicarboxyethylene unit, one of the carboxyl groups of which has been reacted with a polyamine containing one or more primary or secondary amine groups.

The most particularly preferred amphoteric fixing polymers corresponding to the definition given above are chosen from the following polymers:

1) polymers resulting from the copolymerization of a monomer derived from a vinyl compound carrying a carboxyl group, such as more particularly acrylic acid, methacrylic acid, maleic acid or α-chloracrylic acid, and of a basic monomer derived from a substituted vinyl compound containing at least one basic atom, such as more particularly dialkylaminoalkyl methacrylate and acrylate or dialkylaminoalkylmethacrylamide and -acrylamide. Such compounds are described in U.S. Pat. No. 3,836,537.

2) polymers containing units deriving:

a) from at least one monomer chosen from acrylamides or methacrylamides substituted on the nitrogen by an alkyl radical, b) from at least one acidic comonomer containing one or more reactive carboxyl groups, and c) from at least one basic comonomer, such as esters containing primary, secondary, tertiary and quaternary amine substituents of acrylic and methacrylic acids and the quaternization product of dimethylaminoethyl methacrylate with dimethyl or diethyl sulphate.

The more particularly preferred N-substituted acrylamides or methacrylamides according to the invention are the groups in which the alkyl radicals contain from 2 to 12 carbon atoms and more particularly N-ethylacrylamide, N-tert-butylacrylamide, N-tert-octylacrylamide, N-octylacrylamide, N-decylacrylamide or N-dodecylacrylamide, and the corresponding methacrylamides. The acidic comonomers are more particularly chosen from acrylic, methacrylic, crotonic, itaconic, maleic or fumaric acids and alkyl monoesters having 1 to 4 carbon atoms of maleic or fumaric acids or anhydrides. The preferred basic comonomers are aminoethyl, butylaminoethyl, N,N'-dimethylaminoethyl or N-tert-butylaminoethyl methacrylates.

Use is particularly made of the copolymers for which the CT FA name (4 th Ed., 1991) is Octylacrylamide/acrylates/ butylaminoethyl methacrylate copolymer, such as the products sold under the name Amphomer or Lovocryl 47 by the company National Starch.

(3) partially or completely alkylated and crosslinked polyaminoamides deriving from polyamino-amides of general formula:

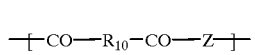

(II)

in which $R_{10}$ represents a divalent radical derived from a saturated dicarboxylic acid, from an aliphatic mono- or dicarboxylic acid containing an ethylenic double bond, from an ester of a lower alkanol having 1 to 6 carbon atoms of these acids, or from a radical deriving from the addition of any one of the said acids with a bisprimary or bissecondary amine, and Z denotes a radical of a bisprimary, mono- or bissecondary polyalkylenepolyamine and preferably represents:

a) in the proportions of 60 to 100 mol %, the radical

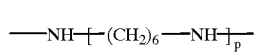

(IV)

where x=2 and p=2 or 3, or else x=3 and p=2 this radical deriving from diethylenetriamine, tri-ethylenetetraamine or dipropylenetriamine;

b) in the proportions of 0 to 40 mol %, the above radical (IV), in which x=2 and p=1 and which derives from ethylenediamine, or the radical deriving from piperazine:

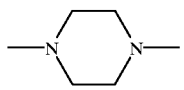

c) in the proportions of 0 to 20 mol %, the radical —NH—(CH$_2$)$_6$—NH— deriving from hexamethylenediamine, these polyaminoamides being crosslinked by an addition reaction of a bifunctional crosslinking agent chosen from epihalohydrins, diepoxides, dianhydrides or bisunsaturated derivatives, by means of 0.025 to 0.35 mol of crosslinking agent per amine group of the polyaminoamide, and reacted acrylic acid, chloracetic acid or an alkanesultone or their salts.

The saturated dicarboxylic acids are preferably chosen from acids having 6 to 10 carbon atoms, such as adipic, 2,2,4-trimethyladipic or 2,4,4-trimethyladipic, or terephthalic acid, and the acids containing an ethylenic double bond are, for example, acrylic, methacrylic or itaconic acids.

The alkanesultones used in the alkylation are preferably propane- or butanesultone and the salts of the alkylating agents are preferably the sodium or potassium salts.

(4) polymers containing zwitterionic units of formula:

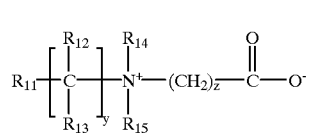

(IV)

in which $R_{11}$ denotes a polymerizable unsaturated group, such as an acrylate, methacrylate, acrylamide or methacrylamide group, y and z represent an integer from 1 to 3, $R_{12}$ and $R_{13}$ represent a hydrogen atom or a methyl, ethyl or propyl radical, and $R_{14}$ and $R_{15}$ represent a hydrogen atom or an alkyl radical such that the sum of the carbon atoms in $R_{14}$ and $R_{15}$ does not exceed 10.

The polymers comprising such units can also contain units derived from non-zwitterionic monomers, such as dimethyl- or diethylaminoethyl acrylate or methacrylate or alkyl acrylates or methacrylates, acrylamides or methacrylamides, or vinyl acetate.

Mention may be made, by way of example, of methyl methacrylate/dimethylcarboxymethylammonioethyl methacrylate copolymer, such as the product sold under the name Diaformer Z301 by the company Sandoz.

(5) polymers derived from chitosan containing monomer units corresponding to the following formulae:

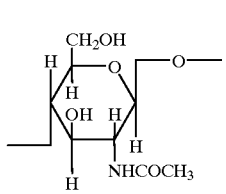

(D)

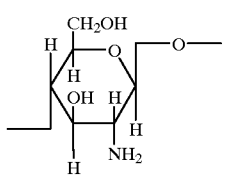

(E)

-continued

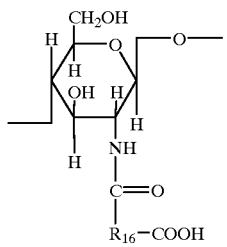
(F)

the unit D being present in proportions of between 0 and 30%, the unit E in proportions of between 5 and 50% and the unit F in proportions of between 30 and 90%, it being understood that, in this unit F, $R_{16}$ represents a radical of formula:

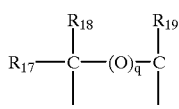

in which, if q=0, $R_{17}$, $R_{18}$ and $R_{19}$, which are identical or different, each represent a hydrogen atom, a methyl, hydroxyl, acetoxy or amino residue, a monoalkylamino residue or a dialkylamino residue, optionally interrupted by one or more nitrogen atoms and/or optionally substituted by one or more amino, hydroxyl, carboxy, alkylthio or sulpho groups, or an alkylthio residue in which the alkyl group carries an amino residue, at least one of the $R_{17}$, $R_{18}$ and $R_{19}$ radicals being, in this case, a hydrogen atom;

or, if q=1, $R_{17}$, $R_{16}$ and $R_{19}$ each represent a hydrogen atom, and the salts formed by these compounds with bases or acids.

(6) polymers derived from the N-carboxyalkylation of chitosan, such as the N-(carboxymethyl)chitosan or the N-(carboxybutyl)chitosan sold under the name "Evalsan" by the company Jan Dekker.

(7) polymers corresponding to the general formula (V) are, for example, described in French Patent 1,400,366:

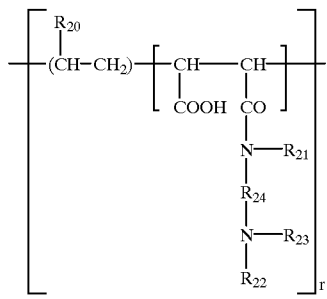
(V)

in which $R_{20}$ represents a hydrogen atom or a $CH_3O$, $CH_3CH_2O$ or phenyl radical, $R_{21}$ denotes hydrogen or a lower alkyl radical such as methyl or ethyl, $R_{22}$ denotes hydrogen or a lower $C_1$–$C_6$ alkyl radical such as methyl or ethyl and $R_{23}$ denotes a lower $C_1$–$C_6$ alkyl radical such as methyl or ethyl or a radical corresponding to the formula: —$R_{24}$—$N(R_{22})_2$, $R_{24}$ representing a —$CH_2$—$CH_2$—, —$CH_2$—$CH_2$—$CH_2$— or —$CH_2$—$CH(CH_3)$— group and $R_{22}$ having the meanings mentioned above.

(8) amphoteric polymers of the —D—X—D—X— type chosen from:

a) Polymers obtained by reaction of chloracetic acid or sodium chloracetate with compounds containing at least one unit of formula:

—D—X—D—X—D— (VI)

where D denotes a radical

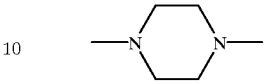

and X denotes the symbol E or E', E or E', which are identical or different, denoting a bivalent radical which is a straight- or branched-chain alkylene radical containing up to 7 carbon atoms in the main chain which is unsubstituted or substituted by hydroxyl groups and which can additionally contain oxygen, nitrogen or sulphur atoms or 1 to 3 aromatic and/or heterocyclic rings; the oxygen, nitrogen and sulphur atoms being present in the form of ether, thioether, sulphoxide, sulphone, sulphonium, alkylamine or alkenylamine groups or hydroxyl, benzylamine, amine oxide, quaternary ammonium, amide, imide, alcohol, ester and/or urethane groups.

b) polymers of formula:

—D—X—D—X— (VI')

where D denotes a radical

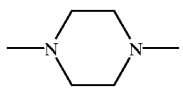

and X denotes the symbol E or E' and E' at least once, E having the meaning indicated above and E' being a bivalent radical which is a straight- or branched-chain alkylene radical having up to 7 carbon atoms in the main chain which is substituted or unsubstituted by one or more hydroxyl radicals and which contains one or more nitrogen atoms, the nitrogen atom being substituted by an alkyl chain optionally interrupted by an oxygen atom and necessarily containing one or more carboxyl functional groups and one or more hydroxyl functional groups and betainized by reaction with chloracetic acid or sodium chloracetate.

(9) ($C_1$–$C_5$)alkyl vinyl ether/maleic anhydride copolymers partially modified by semiamidation with an N,N-dialkylaminoalkylamine, such as N,N-dimethylaminopropylamine, or by semiesterification with an N,N-dialkylaminoalkanol. These copolymers can also contain other vinyl comonomers, such as vinylcaprolactam.

The particularly preferred amphoteric fixing polymers according to the invention are those of the family (3), such as the copolymers with the CTFA name of Octylacrylamide/acrylates/butylaminoethyl methacrylate copolymer, such as the products sold under the names Amphomer, Amhomer LV 71 or Lovocryl 47 by the company National Starch, and those of the family (4), such as methyl methacrylate/dimethylcarboxymethylammonioethyl methacrylate copolymers, for example sold under the name Diaformer Z301 by the company Sandoz.

The non-ionic fixing polymers which can be used according to the present invention are chosen, for example, from polyalkyloxazolines, such as the polyethyloxazolines provided by the company Dow Chemical under the names PEOX 50 000, PEOX 200 000 and PEOX 500 000;

vinyl acetate homopolymers, such as the product provided under the name Appretan EM by the company Hoechst or the product provided under the name Rhodopas A 012 by the company Rhone-Poulenc;

copolymers of vinyl acetate and of acrylic ester, such as the product provided under the name Rhodopas AD 310 from Rhône-Poulenc;

copolymers of vinyl acetate and of ethylene, such as the product provided under the name Appretan TV by the company Hoechst;

copolymers of vinyl acetate and of maleic ester, for example of dibutyl maleate, such as the product provided under the name Appretan MB Extra by the company Hoechst;

vinyl chloride homopolymers, such as the products provided under the names Geon 460X45, Geon 460X46 and Geon 577 by the company Goodrich;

polyethylene waxes, such as the products provided under the names Aquacer 513 and Aquacer 533 by the company Byk Cera;

polyethylene/polytetrafluoroethylene waxes, such as the products provided under the names Drewax D-3750 by the company Drew Ameroid and Wax Dispersion WD-1077 by the company R. T. Newey;

alkyl acrylate homopolymers and alkyl methacrylate homopolymers, such as the product provided under the name Micropearl RQ 750 by the company Matsumoto and the product provided under the name Luhydran A 848 S by the company BASF;

acrylic ester copolymers, such as, for example, copolymers of alkyl acrylates and of alkyl methacrylates, such as the products provided by the company Rohm & Haas under the names Primal AC-261 K and Eudragit NE 30 D, by the company BASF under the names Acronal 601, Luhydran R 8833 or 8845, or by the company Hoechst under the names Appretan N 9213 or N9212;

copolymers of acrylonitrile and of a non-ionic monomer chosen, for example, from butadiene and alkyl (meth) acrylates; mention may be made of the products provided under the names Nipol LX 531 B by the company Nippon Zeon or those provided under the name CJ 0601 B by the company Rohm & Haas;

styrene homopolymers, such as the product Rhodopas 5051 provided by the company Rhône-Poulenc;

copolymers of styrene and of alkyl (meth)acrylate, such as the products Mowilith LDM 6911, Mowilith DM 611 and Mowilith LDM 6070 provided by the company Hoechst or the products Rhodopas SD 215 and Rhodopas DS 910 provided by the company Rhône-Poulenc;

copolymers of styrene, of alkyl methacrylate and of alkyl acrylate, such as the product Daitisol SPA provided by the company Wackherr;

copolymers of styrene and of butadiene, such as the products Rhodopas SB 153 and Rhodopas SB 012 provided by the company Rhône-Poulenc;

copolymers of styrene, of butadiene and of vinylpyridine, such as the products Goodrite SB Vinylpyridine 2528X10 and Goodrite SB Vinylpyridine 2508 provided by the company Goodrich;

polyurethanes, such as the products provided under the names Acrysol RM 1020 or Acrysol RM 2020 by the company Rohm & Haas or the products Uraflex XP 401 UZ or Uraflex XP 402 UZ by the company DSM Resins;

copolymers of alkyl acrylate and of urethane, such as the product 8538-33 by the company National Starch;

polyamides, such as the product Estapor LO 11 provided by the company Rhône-Poulenc;

chemically modified or unmodified non-ionic guar gums.

The unmodified non-ionic guar gums are, for example, the products sold under the name Vidogum GH 175 by the company Unipectine and under the name Jaguar C by the company Meyhall.

The modified non-ionic guar gums which can be used according to the invention are preferably modified by $C_1$–$C_6$ hydroxyalkyl groups. Mention may be made, by way of example, of the hydroxymethyl, hydroxyethyl, hydroxypropyl and hydroxybutyl groups.

These guar gums are well known in the state of the art and can, for example, be prepared by reacting the corresponding alkene oxides, such as, for example, propylene oxides, with guar gum, so as to obtain a guar gum modified by hydroxypropyl groups.

Such non-ionic guar gums optionally modified by hydroxyalkyl groups are, for example, sold under the trade names Jaguar HP8, Jaguar HP60 and Jaguar HP120, Jaguar DC 293 and Jaguar HP 105 by the company Meyhall or under the name Galactasol 4H4FD2 by the company Aqualon.

The alkyl radicals of the non-ionic polymers mentioned above preferably have from 1 to 6 carbon atoms.

According to the invention, it is also possible to use fixing polymers of grafted silicone type comprising a polysiloxane portion and a portion composed of a non-silicone organic chain, one of the two portions constituting the main chain of the polymer and the other being grafted onto the said main chain. These polymers are described, for example, in Patent Applications EP-A-0,412,704, EP-A-0,412,707, EP-A-0,640,105 and WO 95/00578, EP-A-0,582,152 and WO 93/23009 and Patents U.S. Pat. No. 4,693,935, U.S. Pat. No. 4,728,571 and U.S. Pat. No. 4,972,037. These polymers are preferably anionic or non-ionic.

Such polymers are, for example, the copolymers capable of being obtained by radical polymerization from the mixture of monomers composed of:

a) 50 to 90% by weight of tert-butyl acrylate;

b) 0 to 40% by weight of acrylic acid;

c) 5 to 40% by weight of silicone macromer of formula:

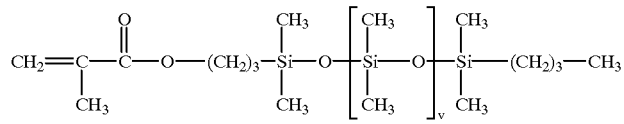

with v being a number ranging from 5 to 700, the percentages by weight being calculated with respect to the total weight of the monomers.

Other examples of grafted silicone polymers are in particular polydimethylsiloxanes (PDMS) on which are grafted, via a connecting link of thiopropylene type, mixed polymer units of the poly(meth)acrylic acid type and of the poly(alkyl (meth)acrylate) type and polydimethylsiloxanes (PDMS) on which are grafted, via a connecting link of thiopropylene type, polymer units of the poly(isobutyl (meth)acrylate) type.

According to the present invention, the fixing polymers are preferably anionic polymers.

The amphoteric or anionic fixing polymers can, if necessary, be partially or completely neutralized. The neutralization agents are, for example, sodium hydroxide, potassium hydroxide, 2-amino-2-methyl-1-propanol, monoethanolamine, triethanolamine or triisopropanolamine, or inorganic or organic acids, such as hydrochloric acid or citric acid.

The compositions according to the invention in addition necessarily comprise at least one oxyalkylenated silicone.

According to the invention, oxyalkylenated silicone denotes any silicone containing at least one oxyalkylene group of (—$C_xH_{2x}O$) a type in which x can vary from 2 to 6 and a is greater than or equal to 1.

In all which follows or which precedes, silicone is understood to denote, in accordance with the general meaning, all organosilicon polymers or oligomers with a branched or crosslinked, linear or cyclic structure, of variable molecular weight, obtained by polymerization and/or polycondensation of suitably functionalized silanes and essentially composed of a repetition of main units in which the silicon atoms are connected to one another via oxygen atoms (siloxane bond ≡Si—O—Si≡), optionally substituted hydrocarbon radicals being bonded directly via a carbon atom to the said silicon atoms. The most common hydrocarbon radicals are alkyl radicals, especially $C_1$–$C_{10}$ alkyl radicals and in particular the methyl radical, fluoroalkyl radicals or aryl radicals and in particular the phenyl radical.

The oxyalkylenated silicones are chosen, for example, from compounds of general formulae (VII), (VIII), (IX), (X) and (XI):

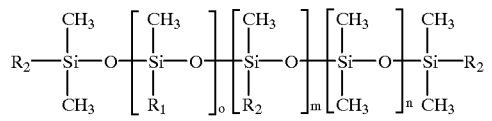
(VII)

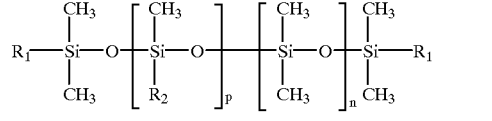
(VIII)

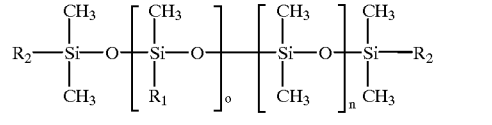
(IX)

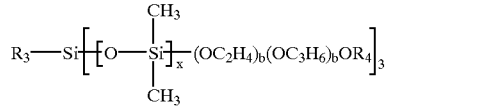
(X)

in which formulae:

$R_1$, which is identical or different, represents a linear or branched $C_1$–$C_{30}$ alkyl or phenyl radical, $R_2$, which is identical or different, represents a —$C_cH_{2c}$—O—$(C_2H_4O)_a(C_3H_6O)_b$—$R_5$ radical or a —$C_cH_{2c}$—O—$(C_4H_8O)_a$—$R_5$ radical, $R_3$ and $R_4$, which are identical or different denote a linear or branched $C_1$–$C_{12}$ alkyl radical and preferably the methyl radical, $R_5$, which is identical or different, is chosen from a hydrogen atom, a linear or branched alkyl radical containing 1 to 12 carbon atoms, a linear or branched alkoxy radical containing 1 to 6 carbon atoms, a linear or branched acyl radical containing 2 to 12 carbon atoms, a hydroxyl, —$SO_3M$, —$OCOR_6$, $C_1$–$C_6$ aminoalkoxy, optionally substituted on the amine, $C_2$–$C_6$ aminoacyl, optionally substituted on the amine, —$NHCH_2CH_2COOM$, —$N(CH_2CH_2COOM)_2$, aminoalkyl, optionally substituted on the amine and on the alkyl chain, or $C_2$–$C_{30}$ carboxyacyl radical or a phosphono, optionally substituted by one or two substituted aminoalkyl radicals, —$CO(CH_2)_dCOOM$, —$OCOCHR_7(CH_2)_dCOOM$, —$NHCO(CH_2)_dOH$ or —$NH_3Y$ group, M, which is identical or different, denotes a hydrogen atom, Na, K, Li, $NH_4$ or an organic amine, $R_6$ denotes a linear or branched $C_1$—$C_{30}$ alkyl radical, $R_7$ denotes a hydrogen atom or an $SO_3M$ radical, d varies from 1 to 10, m varies from 0 to 20, n varies from 0 to 500, o varies from 0 to 20, p varies from 1 to 50, a varies from 0 to 50, b varies from 0 to 50, a+b is greater than or equal to 1, c varies from 0 to 4, x varies from 1 to 100, Y represents a monovalent inorganic or organic anion, such as halide (chloride or bromide), sulphate or carboxylate (acetate, lactate or citrate).

Use is preferably made of oxyalkylenated silicones corresponding to the general formulae (VII) or (VIII). More particularly, these formulae meet at least one of and preferably all the following conditions:

c is equal to 2 or 3, $R_1$ denotes the methyl radical, $R_5$ represents a hydrogen atom, a methyl radical or an acetyl radical and preferably a hydrogen atom, a varies from 1 to 25 and more particularly from 2 to 15, b is equal to 0, n varies from 0 to 100, p varies from 1 to 20.

Such silicones are, for example, sold by the company Goldschmidt under the trade names Abil WE 09, Abil EM 90, Abil B8852, Abil B8851, Abil B 8843 or Abil B 8842, by the company Dow Corning under the names Fluid DC 190, Dow Corning 193, DC 3225 C, Q2-5220, Q2-5354 or Q2-5200, by the company Rhone-Poulenc under the names Silbione Oil 70646 or Rhodorsil Oil 10634, by the company General Electric under the names SF1066 or SF1188, by the company SWS Silicones under the name Silicone Copolymer F 754, by the company Amerchol under the name Silsoft Beauty Aid SL, by the company Shin-Etsu under the name KF 351, by the company Wacker under the name Belsil DMC 6038, by the company Siltech under the names Silwax WD-C, Silwax WD-B, Silwax WD-IS, Silwax WS-L, Silwax DCA 100 or Siltech Amine 65 or by the company Fanning Corporation under the names Fancorsil SLA or Fancorsil LIM1.

The oxyalkylenated silicones can also be chosen from silicones of following formula (XI):

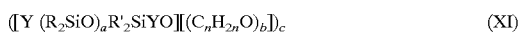
(XI)

in which formula:

R and R', which are identical or different, represent a monovalent hydrocarbon radical, n is an integer ranging from 2 to 4, a is a number greater than or equal to 4, preferably of between 4 and 200 and more particularly still between 4 and 100, b is a number greater than or equal to 4, preferably of between 4 and 200 and more particularly still between 5 and 100, c is a number greater than or equal to 4, preferably of between 4 and 1000 and more particularly still between 5 and 300, Y represents a divalent organic group which is bonded to the adjacent silicon atom via a carbon-silicon bond and to a polyoxyalkylene block via an oxygen atom, the average molecular weight of each siloxane block is between approximately 400 and approximately 10,000, that of each polyoxyalkylene block being between approximately 300 and approximately 10,000, the siloxane blocks represent from approximately 10% to approximately 95% by weight of the block copolymer, it being possible for the number-average molecular weight of the block copolymer to arrange from 2500 to 1 million and preferably between 3000 and 200,000 and more particularly still between 6000 and 100,000.

R and R' are preferably chosen from the group comprising linear or branched alkyl radicals, such as, for example, the methyl, ethyl, propyl, butyl, pentyl, hexyl, octyl, decyl or dodecyl radicals, aryl radicals, such as, for example, phenyl or naphthyl, or aralkyl or alkylaryl radicals, such as, for example, benzyl, phenylethyl or the tolyl or xylyl radicals.

Y is preferably —R"—, —R"—CO—, —R"—NHCO—, —R"—NH— CO—NH—R"—NHCO— or —R"—OCONH—R"'—NHCO—, where R" is a linear or branched divalent $C_1$–$C_6$ alkylene group, such as, for example, ethylene, propylene or butylene, which is linear or branched, and R"' is a divalent alkylene group or a divalent arylene group, such as —$C_6H_4$—, —$C_6H_4$—$C_6H_4$—, —$C_6H_4$—$CH_2$—$C_6H_4$— or —$C_6H_4$—$C(CH_3)_2$—$C_6H_4$—.

More preferably still, Y represents a divalent alkylene radical, more particularly the —$CH_2$—$CH_2$—$CH_2$— radical or the linear or branched $C_4H_8$ radical.

The preparation of the block copolymers employed in the context of the present invention is described in European Application EP 0,492,657 A1, the teaching of which is included by reference in the present description.

Preferred oxyalkylenated silicones according to the invention can be chosen from those of formula (XII):

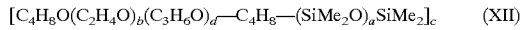

in which:
Me represents methyl,
a is a number between 4 and 100,
b and d, which are identical or different, are numbers ranging from 0 to 100,
c is a number ranging from 5 to 300,
b+d is a number ranging from 1 to 200.

Polymers for which the repeat unit is of formula (XII) and for which the siloxane/poly-oxyalkylene ratio by weight is approximately 75/25 and the polyoxyethylene/polyoxypropylene ratio by weight is approximately 50/50, polymers for which the siloxane/polyoxyalkylene ratio by weight is approximately 35/65 and the polyoxyethylene/poly-oxypropylene ratio by weight is approximately 100/0, polymers for which the siloxane/polyoxyalkylene ratio by weight is approximately 30/70 and the polyoxyethylene/polyoxypropylene ratio by weight is approximately 0/100 and more particularly those for which the siloxane/polyoxyalkylene ratio by weight is approximately 20/80 and the polyoxyethylene/poly-oxypropylene ratio by weight is approximately 65/35 are preferably chosen.

Such products are sold, for example, under the name Silicone Fluid FZ-2172 by the company OSI.

The compositions according to the invention also comprise, as essential component, at least one water-soluble solvent with a boiling point of less than 85° C.

Water-soluble solvent is understood to mean, according to the present invention, a solvent soluble to more than 5% by weight in water.

The water-soluble solvent having a boiling point of less than 85° C. can more particularly be chosen from $C_2$–$C_6$ alcohols, preferably ethanol, tert-butanol or isopropanol.

The water-soluble solvent or solvents having a boiling point of less than 85° C. must be present in concentrations of greater than or equal to 30%, generally of between 30 and 60% and preferably between 40 and 55%, these concentrations being expressed by weight with respect to the total weight of the composition, without taking into account the propellant.

The fixing polymer or polymers can be present in proportions of between 5 and 40% by weight with respect to the total weight of the composition, without taking into account the propellant, and preferably between 6 and 15% by weight.

The oxyalkylenated silicone or silicones can be present in the compositions according to the invention in proportions of between 0.01 and 10% by weight with respect to the total weight of the composition, without taking into account the propellant, and preferably between 0.05 and 5% by weight.

The water-soluble solvent/oxyalkylenated silicone ratio by weight is preferably between 0.01 and 1.

According to the invention, for the purpose of obtaining an aerosol foam, the composition comprises at least one conventional propellant which can be chosen from volatile hydrocarbons, such as n-butane, propane or isobutane, chlorinated and/or fluorinated hydrocarbons and their mixtures. It is also possible to use, as propellant, carbon dioxide gas, nitrous oxide, dimethyl ether, nitrogen, compressed air and their mixture.

The propellant or propellants are generally present in the compositions according to the invention in concentrations of between 1 and 20% by weight with respect to the total weight of the composition in the pressurized state and preferably between 5 and 15% by weight.

The cosmetically acceptable medium can contain, in addition to the solvent or solvents having a boiling point of less than 85° C., other cosmetically acceptable solvents, such as water, polyalcohols, glycol ethers or fatty acid esters, which can be used alone or as a mixture.

Mention may more particularly be made of polyalcohols, such as diethylene glycol, or glycol ethers, such as glycol or diethylene glycol or propylene glycol monoalkyl ethers.

Water is generally present in the compositions according to the invention. This water can be present in concentrations of between 20 and 65% by weight with respect to the total weight of the composition, the propellant system not included.

The pH of the compositions according to the invention is generally between 2 and 10 and particularly between 3 and 8. It can be adjusted to the chosen value by means of basifying or acidifying agents commonly used in cosmetics for this type of application.

The compositions according to the invention can also contain thickening agents, surface-active agents, preservatives, sequestering agents, softeners, fragrances, dyes, viscosity-modifying agents, foam-modifying agents, foam stabilizers, pearlescent agents, moisturizing agents, agents for combating dandruff, antiseborrhoeic agents, sunscreens, proteins, vitamins, plasticizers, hydroxy acids, electrolytes and fragrances.

The compositions according to the invention can also contain conditioning agents. The latter can then be chosen from natural or synthetic oils and waxes, fatty alcohols, esters of polyhydric alcohols, glycerides, silicone oils, gums and resins or mixtures of these various compounds.

Of course, a person skilled in the art will take care to choose the optional compound or compounds to be added to the composition according to the invention so that the advantageous properties intrinsically attached to the composition in accordance with the invention are not, or not substantially, detrimentally affected by the envisaged addition.

A further subject of the invention is a process for the cosmetic treatment of keratinous fibres, such as hair or eyelashes, characterized in that it consists in applying, to keratinous fibres, a foam resulting from the expansion in the air of the cosmetic composition as defined above.

The cosmetic compositions according to the invention can be provided in the form of more or less thickened solutions, of dispersions or of emulsions capable of forming a foam.

In all which follows or which precedes, the percentages are expressed, except when otherwise mentioned, by weight with respect to the weight of the composition not containing the propellant.

The invention will now be more fully illustrated using the following examples, which should not be regarded as limiting it to the embodiments described. In these examples, AM means active material.

EXAMPLE 1

A styling foam (A) was prepared with the following composition:

| | |
|---|---|
| Vinyl acetate/vinyl p-tert-butylbenzoate/crotonic acid terpolymer (fixing polymer) | 8 g |
| 2-Amino-2-methyl-1-propanol (q.s. 100% neutralization of the fixing polymer) | 0.8 g |
| Ethanol | 49.5 g |
| Oxyalkylenated silicone sold under the name Silicone Fluid FZ-2172 by the company OSI | 1.05 g AM |
| Water q.s. for | 100 g |

Aerosol packaging:

90 g of the above composition are packaged in a conventional aerosol container in the presence of 10 g of a ternary mixture of n-butane, isobutane and propane (23/55/22) sold under the name "Aérogaz 3,2 N" by the company Elf Aquitaine.

A beautiful foam is obtained at the outlet of the aerosol device. An amount of foam equivalent in size to a tangerine is removed, spread quickly over the hands and then applied using the hands to washed and dried hair while shaping the hair.

The hairstyle is quickly prepared and exhibits good hold and volume. The hair is glossy and without residues and the feel is natural.

Comparative Examples

A composition (B) not in accordance with the invention was prepared by replacing, in the composition of Example 1, the Silicone Fluid FZ-2172 copolymer by the same amount of a surfactant used conventionally as foaming agent in the foams of the prior art, namely nonylphenol oxyethylenated with 9 mol of ethylene oxide (Igepal NP 9 from Rhone-Poulenc).

The composition (B) is subsequently pressurized in the same way as the composition (A). Foam is not obtained at the outlet of the aerosol device.

A composition (C) not in accordance with the invention was prepared by replacing, in the composition of Example 1, the Silicone Fluid FZ-2172 copolymer by the same amount of a polymer used conventionally as foaming agent in the foams of the prior art, namely the copolymer of vinyl alcohol and of vinyl acetate (Covol 9740 from CPC International).

The composition (C) is subsequently pressurized in the same way as the composition (A). Foam is not obtained at the outlet of the aerosol device.

Compositions (B') and (C'), similar to the compositions (B) and (C) but in which the ethanol content was reduced to approximately 15%, were prepared. The compositions were pressurized in an aerosol device as above. A foam was obtained at the outlet of the aerosol device.

The foams resulting from the two compositions (B') and (C'), not in accordance with the invention, were subsequently tested on hair.

An amount of foam equivalent in size to a tangerine was removed, spread quickly over the hands and then applied using the hands to washed and dried hair. The two foams wet the hair but the shaping of the hair requires blow-drying. The hairstyle volume is low.

EXAMPLE 2

A styling foam was prepared with the following composition:

| | |
|---|---|
| Acrylic acid/ethyl acrylate/N-tert-butylacrylamide terpolymer sold under the name Ultrahold Strong by the company BASF (fixing polymer) | 8 g |
| 2-Amino-2-methyl-1-propanol (q.s. 100% neutralization of the fixing polymer) | 0.8 g |
| Ethanol | 49.5 g |
| Oxyalkylenated silicone sold under the name Silicone Fluid FZ-2172 by the company OSI | 2.14 g AM |
| Water q.s. for | 100 g |

Aerosol packaging:

90 g of the above composition are packaged in an aerosol container in the presence of 10 g of a ternary mixture of n-butane, isobutane and propane (23/55/22) sold under the name "Aérogaz 3,2 N" by the company Elf Aquitaine.

EXAMPLE 3

A styling foam was prepared with the following composition:

| | |
|---|---|
| Acrylic acid/ethyl acrylate/N-tert-butylacrylamide terpolymer sold under the name Ultrahold Strong by the company BASF (fixing polymer) | 8 g |
| 2-Amino-2-methyl-1-propanol | 0.8 g |

| | |
|---|---|
| (q.s. 100% neutralization of the fixing polymer) | |
| Ethanol | 49.5 g |
| Oxyalkylenated silicone sold under the name Silicone Fluid FZ-2172 by the company OSI | 0.07 g AM |
| Water q.s. for | 100 g |

Aerosol packaging:

90 g of the above composition are packaged in an aerosol container in the presence of 10 g of a ternary mixture of n-butane, isobutane and propane (23/55/22) sold under the name "Aérogaz 3,2 N" by the company Elf Aquitaine.

EXAMPLE 4

A styling foam was prepared with the following composition:

| | |
|---|---|
| Acrylic acid/ethyl acrylate/ N-tert-butylacrylamide terpolymer sold under the name Ultrahold Strong by the company BASF (fixing polymer) | 8 g |
| 2-Amino-2-methyl-1-propanol (q.s. 100% neutralization of the fixing polymer) | 0.8 g |
| Ethanol | 43 g |
| Oxyethylenated and oxypropylenated silicone of formula (II) sold by the company Dow Corning under the name Fluid DC 190 | 4 g |
| Water q.s. for | 100 g |

Aerosol packaging:

90 g of the above composition are packaged in an aerosol container in the presence of 10 g of a ternary mixture of n-butane, isobutane and propane (23/55/22) sold under the name "Aérogaz 3,2 N" by the company Elf Aquitaine.

EXAMPLE 5

A styling foam was prepared with the following composition:

| | |
|---|---|
| Vinyl acetate/vinyl p-tert-butylbenzoate/ crotonic acid terpolymer sold under the name Mexomer PW by the company Chimex (fixing polymer) | 8 g |
| 2-Amino-2-methyl-1-propanol (q.s. 100% neutralization of the fixing polymer) | 0.8 g |
| Ethanol | 49.5 g |
| Oxyethylenated silicone of formula (II) sold by the company Goldschmidt under the name Abil B 8842 | 2 g |
| Water q.s. for | 100 g |

Aerosol packaging:

90 g of the above composition are packaged in an aerosol container in the presence of 10 g of a ternary mixture of n-butane, isobutane and propane (23/55/22) sold under the name "Aérogaz 3,2 N" by the company Elf Aquitaine.

The compositions of Examples 2 to 5 above gave results equivalent to those obtained with the composition according to the invention of Example 1.

We claim:

1. A cosmetic composition pressurized in an aerosol device in the presence of at least one foam-forming propellant, comprising, in a cosmetically acceptable medium, at least one fixing polymer, at least one oxyalkylenated silicone and at least 30% by weight, relative to the total weight of said composition, said propellant not included, of at least one water-soluble solvent with a boiling point of less than 85° C.

2. A cosmetic composition according to claim 1, wherein said at least one oxyalkylenated silicone is selected from compounds of formulae (VII), (VIII), (IX) and (X):

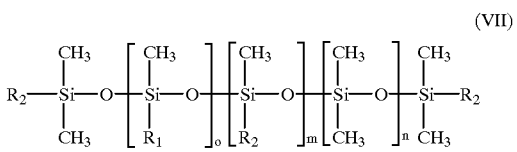

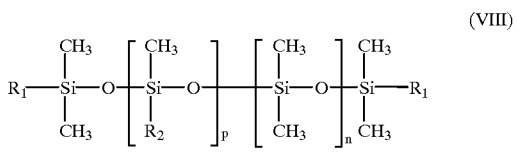

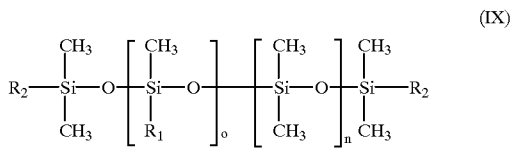

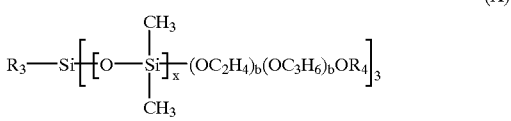

in which:

$R_1$ independently represents a linear or branched $C_1$–$C_{30}$ alkyl or phenyl radical, $R_2$ independently represents a —$C_cH_{2c}$—O—$(C_2H_4O)_a$ $(C_3H_6O)_b$—$R_5$ radical or a —$C_cH_{2c}$—O—$(C_4H_8O)_a$— $R_5$ radical, $R_3$ and $R_4$ independently denote a linear or branched $C_1$—$C_{12}$ alkyl radical, $R_5$ is independently selected from a hydrogen atom, a linear or branched alkyl radical having 1 to 12 carbon atoms, a linear or branched alkoxy radical containing 1 to 6 carbon atoms, a linear or branched acyl radical having 2 to 12 carbon atoms, a hydroxyl, —$SO_3M$, —$OCOR_6$, $C_1$-$C_6$ aminoalkoxy, optionally substituted on the amine, $C_2$-$C_6$ aminoacyl, optionally substituted on the amine, —$NHCH_2CH_2COOM$, —$N(CH_2CH_2COOM)_2$, aminoalkyl, optionally substituted on the amine and on the alkyl chain, and $C_2$–$C_{30}$ carboxyacyl radical or a phosphono, optionally substituted by one or two substituted aminoalkyl radicals, —$CO(CH_2)_dCOOM$, —$OCOCHR_7(CH_2)_dCOOM$, —$NHCO(CH_2)_dOH$ or —$NH_3Y$ group, M independently denotes a hydrogen atom, Na, K, Li, $NH_4$ or an organic amine, $R_6$ denotes a linear or branched $C_1$–$C_{30}$ alkyl radical, $R_7$ denotes a hydrogen atom or an $SO_3M$ radical, d independently ranges from 1 to 10, m ranges from 0 to 20, n independently ranges from 0 to 500, o independently ranges from 0 to 20, p ranges from 1 to 50, a independently ranges from 0 to 50, b independently ranges from 0 to 50, a+b is greater than or equal to 1, c independently ranges from 0 to 4, x ranges from 1 to 100, and Y independently represents a monovalent inorganic or organic anion.

3. A cosmetic composition according to claim 2, wherein at least one of the following conditions is true:

$R_3$ and/or $R_4$ independently represent a methyl radical and

Y independently denotes a halide, sulphate or carboxylate.

4. A cosmetic composition according to claim 2, wherein said at least one oxyalkylenated silicone is selected from compounds of formula (III) and (VIII).

5. A cosmetic composition according to claim 4, wherein at least one of the following conditions is true:

c independently is equal to 2 or 3, $R_1$ denotes the methyl radical, $R_5$ independently represents a hydrogen atom, a methyl radical or an acetyl radical, a independently ranges from 1 to 25, b is equal too, n independently ranges from 0 to 100, p ranges from 1 to 20.

6. A cosmetic composition according to claim 5, wherein $R_5$ represents a hydrogen atom.

7. A cosmetic composition according to claim 5, wherein a independently ranges from 2 to 15.

8. A cosmetic composition according to claim 1, wherein said at least one oxyalkylenated silicone is selected from compounds of formula (XI):

$$([Y(R_2SiO)_aR'_2SiYO][(C_nH_{2n}O)_b])_c \qquad (XI)$$

in which:

$R_2$ and $R'_2$ independently represent a monovalent hydrocarbon radical, n is an integer independently ranging from 2 to 4, a is a number independently greater than or equal to 4, b is a number independently greater than or equal to 4, c is a number independently greater than or equal to 4, Y independently represents a divalent organic group which is bonded to the adjacent silicon atom via a carbon-silicon bond and to a polyoxyalkylene block via an oxygen atom.

9. A cosmetic composition according to claim 8, wherein at least one of the following conditions is true:

a independently ranges from 4 to 200, b independently ranges from 4 to 200, and c independently range s from 4 to 1000.

10. A cosmetic composition according to claim 9, wherein at least one of the following conditions is true:

a independently ranges from 4 to 100, b independently ranges from 5 to 100, and c independently ranges from 5 to 300.

11. A cosmetic composition according to claim 8, wherein $R_2$ and $R'_2$ are independently selected from linear or branched alkyl radicals, aryl radicals and aralkyl radicals; and Y is independently —R'—, —R"—CO—, —R"—NHCO—, —R"—NH—CO—NH—R"—NHCO— or —R"—OCONH—R"'—NHCO—, wherein R" is a linear or branched divalent $C_1$–$C_6$ alkylene group and R"' is a divalent alkylene group or a divalent arylene group.

12. A cosmetic composition according to claim 11, wherein at least one of the following conditions is true:

said linear or branched alkyl radicals are selected from methyl, ethyl, propyl, butyl, pentyl, hexyl, octyl, decyl and dodecyl radicals;

said aryl radicals are selected from phenyl and naphthyl;

said aralkyl radicals are selected from benzyl, phenylethyl and tolyl and xylyl radicals; and R"' is selected from —$C_6H_4$—, —$C_6H_4$—$C_6H_4$—, —$C_6H_4$—$CH_2$—$C_6H_4$— and —$C_6H_4$—$C(CH_3)_2$—$C_6H_4$—.

13. A cosmetic composition according to claim 1, wherein said at least one oxyalkylenated silicone is selected from compounds of formula (XII):

$$[C_4H_8O(C_2H_4O)_b(C_3H_6O)_d\text{—}C_4H_8\text{—}(SiMe_2O)_aSiMe_2]_c \qquad (XII)$$

in which:

Me represents methyl, a is a number independently ranging from 4 to 100, b and d independently represent numbers ranging from 0 to 100, c is a number ranging from 5 to 300, and b+d is a number ranging from 1 to 200.

14. A cosmetic composition according to claim 1, wherein said at least one fixing polymer is selected from anionic, cationic, amphoteric and non-ionic polymers.

15. A cosmetic composition according to claim 14, wherein said anionic polymers are selected from:

polymers containing carboxyl units deriving from unsaturated carboxylic mono- or diacid monomers of formula (I):

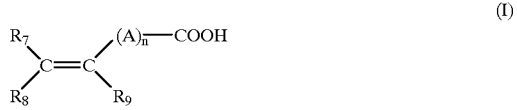

(I)

in which:

n is an integer ranging from 0 to 10,

A denotes a methylene group, optionally bonded to the carbon atom of the unsaturated group or to the neighbouring methylene group when n is greater than 1 via a heteroatom, $R_7$ denotes a hydrogen atom or a phenyl or benzyl group, $R_8$ denotes a hydrogen atom or a lower alkyl or carboxyl group, and $R_9$ denotes a hydrogen atom, a lower alkyl group or a —$CH_2$—COOH, phenyl or benzyl group; and polymers comprising units deriving from sulphonic acid.

16. A cosmetic composition according to claim 15, wherein said lower alkyl group has from 1 to 4 carbon atoms.

17. A cosmetic composition according to claim 16, wherein said lower alkyl group is methyl or ethyl.

18. A cosmetic composition according to claim 15, wherein said units deriving from sulphonic acid are selected from vinylsulphonic, styrenesulphonic and acrylamidoalkylsulphonic units.

19. A cosmetic composition according to claim 15, wherein said heteroatom Is oxygen or sulphur.

20. A cosmetic composition according to claim 15, wherein said anionic polymers are selected from:
  A) homo- or copolymers of acrylic or methacrylic acid and their salts, copolymers of acrylic acid and of acrylamide and their salts, and the sodium salts of polyhydroxycarboxylic acids;
  B) copolymers of acrylic or methacrylic acid with a monoethylenic monomer; wherein said copolymers contain, in their chain, an optionally N-alkylated and/or -hydroxyalkylated acrylamide unit; and copolymers of acrylic acid and of $C_1$–$C_4$ alkyl methacrylate;
  C) copolymers derived from crotonic acid, optionally grafted and crosslinked;
  D) copolymers derived from $C_4$–$C_8$ monounsaturated carboxylic acids or anhydrides selected from:
    copolymers of (i) at least one maleic, fumaric or itaconic acid or anhydride and (ii) at least one monomer selected from vinyl esters, vinyl ethers, vinyl halides, phenylvinyl derivatives, or acrylic acid and its esters, wherein any anhydride functional group of these copolymers is optionally monoesterified or monoamidated;
    copolymers of (i) at least one maleic, citraconic or itaconic anhydride and (ii) at least one monomer selected from allyl or methallyl esters, optionally containing one or more acrylamide, methacrylamide, α-olefin, acrylic or methacrylic ester, acrylic or methacrylic, acid, or vinylpyrrolidone groups in their chain, wherein any anhydride functional group of these copolymers optionally is monoesterified or monoamidated;
  E) polyacrylamides containing carboxylate groups.

21. A cosmetic composition according to claim 20, wherein at least one of the following conditions is true:
  said monoethylenic monomer in (B) is ethylene or styrene, a vinyl ester or ester of acrylic or methacrylic acid, optionally grafted onto a polyalkylene glycol, and optionally crosslinked;
  said copolymers derived from crotonic acid in (C) are selected from those having, in their chain, vinyl acetate or propionate units and optionally other monomers.

22. A cosmetic composition according to claim 21, wherein said polyalkylene glycol in (B) is polyethylene glycol; said optional monomers in (C) are selected from allyl and methallyl esters, vinyl ethers and vinyl esters of a linear or branched saturated carboxylic acid containing a long hydrocarbon chain.

23. A cosmetic composition according to claim 20, wherein said anionic polymers are selected from
  acrylic acid copolymers;
  copolymers derived from crotonic acid;
  polymers derived from maleic, fumaric or itaconic acids or anhydrides with vinyl esters, vinyl ethers, vinyl halides, phenylvinyl derivatives, or acrylic acid and its esters;
  copolymers of methacrylic acid and of methyl methacrylate;
  copolymers of methacrylic acid and of ethyl acrylate
  vinyl acetate/crotonic acid copolymers; and
  vinyl acetate/crotonic acid/polyethylene glycol terpolymers.

24. A cosmetic composition according to claim 23, wherein at least one of the following conditions is true:
  said acrylic acid copolymers are selected from acrylic acid/ethyl acrylate/N-tert-butylacrylamide terpolymers;
  said copolymers derived from crotonic acid are selected from vinyl acetate/vinyl tert-butylbenzoate/crotonic acid terpolymers and crotonic acid/vinyl acetate/vinyl neododecanoate terpolymers; and
  said polymers derived from maleic, fumaric or itaconic acids or anhydrides with vinyl esters, vinyl ethers, vinyl halides, phenylvinyl derivatives, or acrylic acid and its esters, are monoesterified methyl vinyl ether/maleic anhydride copolymers.

25. A cosmetic composition according to claim 14, wherein said amphoteric polymers are selected from polymers having units deriving from:
  a) at least one monomer selected from acrylamides and methacrylamides substituted on the nitrogen by an alkyl radical,
  b) at least one acidic comonomer containing one or more reactive carboxyl groups, and
  c) at least one basic comonomer.

26. A cosmetic composition according to claim 25, wherein said at least one basic comonomer is selected from esters containing primary, secondary, tertiary and quaternary amine substituents of acrylic and methacrylic acids and the quaternization product of dimethylaminoethyl methacrylate with dimethyl or diethyl sulphate.

27. A cosmetic composition according to claim 25, wherein said amphoteric polymers are selected from copolymers with the CTFA name of Octylacrylamide/acrylates/butylaminoethyl methacrylate copolymer and methyl methacrylateldimethylcarboxy-methylammonioethyl methacrylate copolymers.

28. A cosmetic composition according to claim 14, wherein said non-ionic polymers are selected from:
  polyalkyloxazolines;
  vinyl acetate homopolymers;
  copolymers of vinyl acetate and of acrylic ester;
  copolymers of vinyl acetate and of ethylene;
  vinyl chloride homopolymers;
  polyethylene waxes;
  polyethylenelpolytetrafluoroethylene waxes;
  copolymers of polyethylene and of maleic anhydride;
  alkyl acrylate homopolymers and alkyl methacrylate homopolymers;
  acrylic ester copolymers;
  copolymers of acrylonitrile and of a non-ionic monomer;
  styrene homopolymers;
  copolymers of styrene and of alkyl (meth)acrylate;
  copolymers of styrene, of alkyl methacrylate and of alkyl acrylate;
  copolymers of styrene and of butadiene;
  copolymers of styrene, of butadiene and of vinylpyridine;
  copolymers of alkyl acrylate and of urethane.

29. A cosmetic composition according to claim 28, wherein at least one of the following conditions is true:
  said acrylic ester copolymers are copolymers of alkyl acrylates and of alkyl methacrylates;
  and wherein in said copolymers of acrylonitrile and of a non-ionic monomer, said non-ionic monomer is selected from butadiene and alkyl (meth)acrylates.

30. A cosmetic composition according to claim 14, wherein said cationic polymers are selected from:
  copolymers of acrylamide and of dimethylaminoethyl methacrylate quaternized with dimethyl sulphate,
  copolymers of acrylamide and of methacryloyloxyethyltrimethylammonium chloride, copolymers of acrylamide and of methacryloyl-oxyethyltrimethylammonium methyl sulphate, optionally quaternized vinylpyrrolidone/dialkylaminoalkyl acrylate or methacrylate copolymers, dimethylaminoethyl methacrylate/vinylcaprolactam/vinylpyrrolidone terpolymers, and quaternized dimethylaminopropyl methacrylamide/vinylpyrrolidone copolymers.

31. A cosmetic composition according to claim 1, wherein said at least one water-soluble solvent is selected from $C_2$–$C_6$ alcohols.

32. A cosmetic composition according to claim 31, wherein said at least one water-soluble solvent is selected from ethanol, tert-butanol and isopropanol.

33. A cosmetic composition according to claim 1, wherein said at least one water-soluble solvent is present in an amount ranging from 30 to 60% by weight relative to the total weight of said composition, said propellant system not included.

34. A cosmetic composition according to claim 33, wherein said at least one water-soluble solvent is present in an amount ranging from 40 to 55% by weight relative to the total weight of said composition, said propellant system not included.

35. A. A cosmetic composition according to claim 1, wherein said composition further comprises water in an amount ranging from 20 to 65% by weight with respect to the total weight of said composition, said propellant system not included.

36. A cosmetic composition according to claim 1, wherein said at least one foam-forming propellant is selected from volatile hydrocarbons, carbon dioxide gas, nitrous oxide, dimethyl ether, nitrogen, and compressed air.

37. A cosmetic composition according to claim 36, wherein said volatile hydrocarbons are selected from n-butane, propane, isobutane, and chlorinated and fluorinated hydrocarbons.

38. A cosmetic composition according to claim 1, wherein said at least one fixing polymer is present in an amount ranging from 5% to 40% by weight relative to the total weight of said composition, said propellant not included.

39. A cosmetic composition according to claim 38, wherein said at least one fixing polymer is present in an amount ranging from 6% to 15% by weight relative to the total weight of said composition, said propellant not included.

40. A cosmetic composition according to claim 1, wherein said at least one oxyalkylenated silicone is present in an amount ranging from 0.01 to 10% by weight relative to the total weight of said composition, said propellant not included.

41. A cosmetic composition according to claim 40, wherein said at least one oxyalkylenated silicone is present in an amount ranging from 0.05 to 5% by weight relative to the total weight of said composition, said propellant not included.

42. A cosmetic composition according to claim 1, wherein said at least one propellant is present in an amount ranging from 1 to 20% by weight relative to the total weight of said pressurized composition.

43. A cosmetic composition according to claim 42, wherein said at least one propellant is present in an amount ranging from 5 to 15% by weight relative to the total weight of said pressurized composition.

44. A cosmetic composition according to claim 1, wherein said composition further comprises at least one additive selected from: surface-active agents, thickening agents, preservatives, sequestering agents, softeners, dyes, viscosity-modifying agents, foam-modifying agents, foam stabilizers, pearlescent agents, moisturizing agents, agents for combating dandruff, antiseborrhoeic agents, sunscreens, proteins, vitamins, plasticizers, hydroxy acids, electrolytes, fragrances and conditioning agents.

45. A cosmetic composition according to claim 1, wherein the ratio of said at least one water-soluble solvent and at least one oxyalkylenated silicone ranges from 0.01:1 to 1:1.

46. A cosmetic composition according to claim 1, wherein said composition is in the form of a foam which expands in air.

47. A cosmetic composition pressurized in an aerosol device in the presence of at least one foam-forming propellant, comprising, in a cosmetically acceptable medium, at least one fixing polymer, at least one oxyalkylenated silicone and at least 30% by weight, relative to the total weight of said composition, said propellant system not included, of at least one water-soluble solvent with a boiling point of less than 85° C., wherein said at least one oxyalkylenated silicone is present in an amount effective as a foaming agent.

48. A process for the cosmetic treatment of keratinous fibres, comprising applying an effective amount of said composition according to claim 1 to said keratinous fibres.

* * * * *

UNITED STATES PATENT AND TRADEMARK OFFICE
CERTIFICATE OF CORRECTION

PATENT NO. : 6,039,933
DATED : March 21, 2000
INVENTOR(S) : Henri Samain, Isabelle Cretois It is certified that error appears in the above-identified patent and that said Letters Patent is hereby corrected as shown below:

In column 13, line 51 (Formula X) after "$(OC_2H_4)$" change "$_b$" to --$_a$--.

In claim 2, column 20, line 30 (Formula X) after "$(OC_2H_4)$" change "$_b$" to --$_a$--.

In claim 2, column 20, line 46, change "containing" to --having--.

In claim 4, column 21, line 16, change "(III)" to --(VII)--.

In claim 5, column 21, line 25, change "too" to --to 0--.

In claim 11, column 21, penultimate line, change "R'" to --R"--.

In claim 11, column 21, last line, change "R"" to --R'''--.

In claim 23, column 23, line 59, after "acrylate" insert --;--.

Signed and Sealed this

Twenty-seventh Day of February, 2001

Attest:

NICHOLAS P. GODICI

*Attesting Officer*  *Acting Director of the United States Patent and Trademark Office*